United States Patent [19]
Cunningham

[11] Patent Number: 5,832,449
[45] Date of Patent: Nov. 3, 1998

[54] METHOD AND SYSTEM FOR DISPENSING, TRACKING AND MANAGING PHARMACEUTICAL TRIAL PRODUCTS

[76] Inventor: David W. Cunningham, 11929 Eagle Bluff Cir., Raleigh, N.C. 27613

[21] Appl. No.: 556,466

[22] Filed: Nov. 13, 1995

[51] Int. Cl.$^6$ .................................................. G06F 159/00
[52] U.S. Cl. .................................................. 705/3; 705/2
[58] Field of Search .......................... 395/201, 202, 395/203, 228, 601, 610; 235/385, 375; 340/825.29, 825.34; 283/55, 67; 705/1, 2, 3, 28; 707/1, 10

[56] References Cited

U.S. PATENT DOCUMENTS

| | | | |
|---|---|---|---|
| 3,845,278 | 10/1974 | Rex, Jr. | 35/37 |
| 4,827,112 | 5/1989 | Yoshino et al. | 235/380 |
| 4,893,270 | 1/1990 | Beck et al. | 364/918 |
| 5,181,743 | 1/1993 | Lloyd | 283/48.1 |
| 5,542,420 | 8/1996 | Goldman et al. | 128/630 |
| 5,628,530 | 5/1997 | Thornton | 283/67 |

*Primary Examiner*—Frantzy Poinvil
*Attorney, Agent, or Firm*—Rhodes, Coats, & Bennett, LLP

[57] ABSTRACT

A new and improved method of dispensing, tracking and managing pharmaceutical product samples by communicatively linking prescribers and pharmacies to a central computing station. The method entails utilizing product trial media that is exchanged for actual pharmaceutical product. The media is encoded with information that identifies a particular pharmaceutical trial product, such as by magnetic encoding similar to that used with credit cards. The media is distributed to participating medical doctors or prescribers who then activate the media via the central computing station. The prescriber then transfers the activated media to patients who then present the media to participating pharmacies. Before filling the pharmaceutical trial product identified by the media, the pharmacy validates the media via a link with the central computing station. Then, the pharmacy dispenses the prescribed pharmaceutical trial product. The central computing station also includes a database that records data related to the use of the media so that all pharmaceutical trial products can be accounted for.

30 Claims, 14 Drawing Sheets

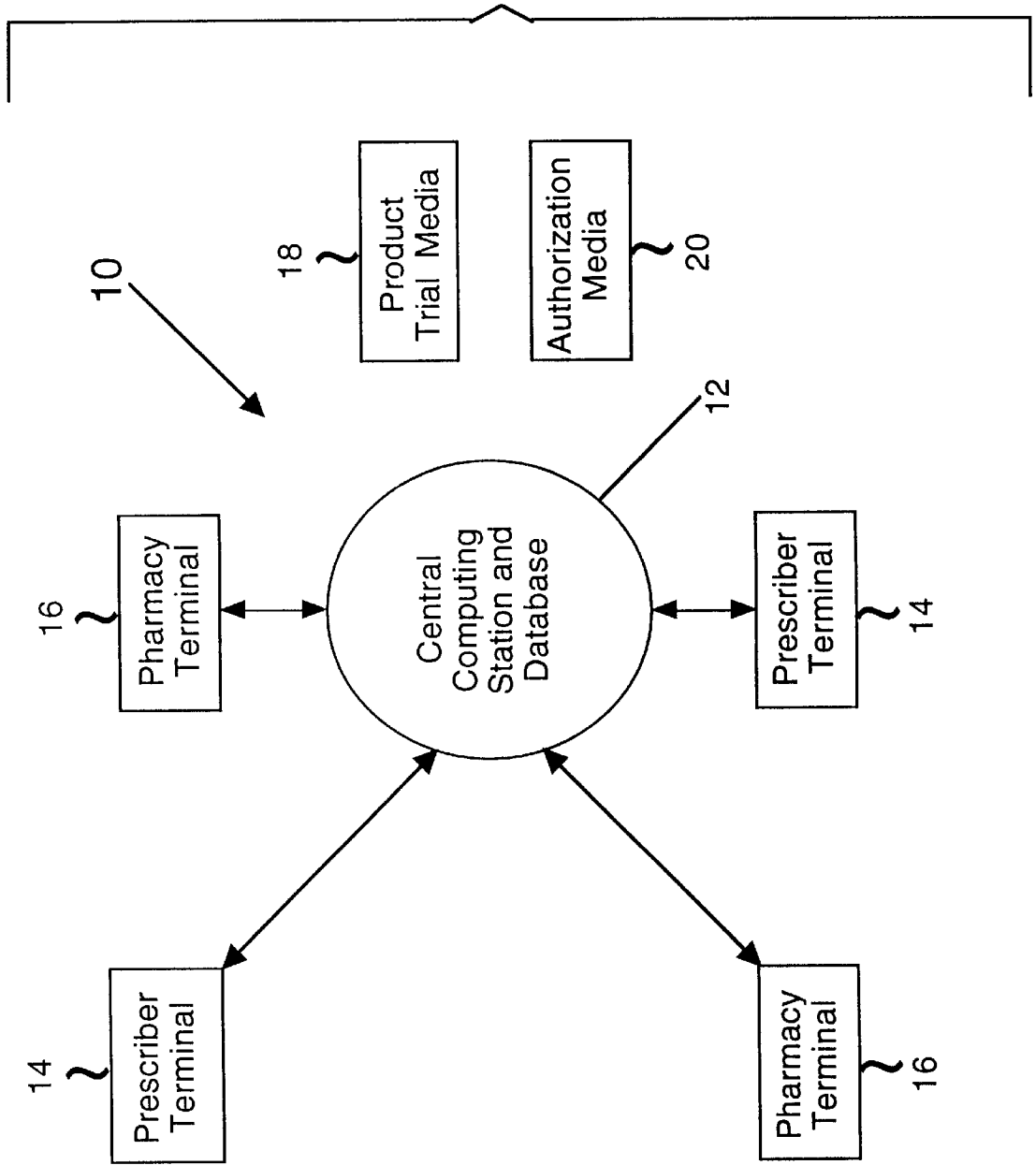

Figure 2A

TRIAL PRODUCT TRADE NAME
TRIAL PRODUCT GENERIC NAME
TRIAL PRODUCT FORM & STRENGTH
TRIAL PRODUCT QUANTITY

CARD SERIAL NUMBER
CARD EXPIRATION DATE

Figure 2B

Physician Approval Code
Pharmacist Approval Code

Physician Signature
Pharmacist Signature
Patient Signature

Figure 3A

AUTHORIZER ID NUMBER

AUTHORIZER NAME
CARD EXPIRATION DATE

Figure 3B

Authorizer Signature

METHOD AND SYSTEM FOR DISPENSING, TRACKING AND MANAGING PHARMACEUTICAL TRIAL PRODUCTS

FIELD OF THE INVENTION

The present invention relates generally to the distribution of pharmaceutical product samples and more particularly to an improved method of dispensing, tracking, and managing pharmaceutical product samples by communicatively linking prescribers and pharmacies to a central computing station.

BACKGROUND OF THE INVENTION

In the pharmaceutical industry, the primary method for product promotion of ethical products is the use of outside sales representatives. Company sales representatives target specific physicians and detail the features and benefits of particular pharmaceutical products. Pharmaceutical manufacturers have documented that the most effective method of product promotion involves providing pharmaceutical product samples to prescribers of the products who then pass along the product samples to patients. Physicians therefore receive numerous quantities of pharmaceutical product samples for purposes of conducting patient trials. These trials enable physicians to determine the effectiveness of certain drugs in certain patients for certain diseases, as well as to determine patients' tolerance of the drugs and their compliance with drug administration directions.

A responsibility of the Food & Drug Administration (FDA) is the regulation of pharmaceutical product samples. The PDMA (Pharmaceutical Drug Manufacturing Act) Act of 1987 requires pharmaceutical manufacturers to track and account for product samples distributed by sales representatives to prescribing physicians. Pharmaceutical manufacturers are required to account for all sample product inventories, as well as the time, location, and specific physicians who receive promotional samples. Pharmaceutical sales representatives are required to record receipts of product samples, adjustments to sample inventories, and distribution of product samples, and to report any loss or theft of product samples. Additionally, PDMA warehousing requirements dictate inventory storage methods and locations both within pharmaceutical companies themselves and for outside pharmaceutical sales representatives.

However, it is often the case that accountability for pharmaceutical product samples ends when the samples reach the physicians. Most physicians do little to account for their inventories of product samples. Rather, physicians tend to distribute pharmaceutical product samples to patients much more informally than retail pharmacies, keeping few if any records and often not even counting the precise number of product samples given to patients.

The PDMA's accountability requirements increase pharmaceutical manufacturers' expenses for promoting and distributing product samples as well as the complexity of administering sampling programs. As competition within the pharmaceutical industry increases, costs associated with product samples place an increasingly greater burden on the pharmaceutical manufacturers. Pharmaceutical manufacturers are therefore attempting to reduce expenses and maintain acceptable profits while incorporating the PDMA's new requirements into established promotional practices.

Although product samples are an extremely effective promotional tool, the manufacturing of drug product samples in addition to normally packaged drug products has proven to be increasingly costly. Pharmaceutical product samples are typically elaborately and expensively packaged and are extremely bulky compared to normally packaged drug products. Pharmaceutical manufacturers must utilize separate product sample packaging lines to specially package drug product samples. Distribution of product samples requires delivery via separate carriers and distribution routes. In addition, drug product samples are typically warehoused separately from normally packaged drug products.

Because the current climate in the pharmaceutical industry prohibits the unrestrained shifting of costs to final consumers, pharmaceutical manufacturers have taken several new approaches to reducing costs associated with promoting product samples. Nevertheless, pharmaceutical manufacturers are attempting to maintain the marketing advantages of using sales representatives to distribute product samples.

One cost-reducing approach that pharmaceutical manufacturers have attempted is the distribution of sample vouchers to prescribing physicians, retail pharmacies, and pharmaceutical sales representatives. With this approach, instead of giving drug product samples directly to patients, physicians give the patients vouchers for the drug product samples. The vouchers may then be redeemed at retail pharmacies for the actual drugs. Alternately, the patients may receive cash or credit rebates at the pharmacies.

Another cost-reducing approach that pharmaceutical manufacturers have attempted is the distribution of product samples via mail order. With this approach, pharmaceutical sales representatives provide prescribing physicians with request authorization forms. Physicians then use the forms to authorize deliveries of product samples directly to physician office from third-party pharmaceutical supply warehouses.

The above new approaches to distributing pharmaceutical product samples have not met with substantial and universal acceptance. All of these approaches lack an effective, efficient and practical system for distributing the trial or sample products to patients and at the same time recording pertinent data, which is easily accessible, relating to prescribing and dispensing the pharmaceutical trial products.

SUMMARY AND OBJECTS OF THE INVENTION

The present invention entails a system and method for managing and tracking the distribution of pharmaceutical trial or sample products by utilizing medical prescribers and pharmacies. Instead of the medical prescriber directly delivering pharmaceutical trial products to patients, the present system and method contemplates the prescriber prescribing a pharmaceutical trial product to a patient and the filling of that prescription by a participating pharmacy. This method and program is managed through a central computing station that is communicatively linked to terminals located at participating prescriber and pharmacy sites. This system, as will be discussed in greater detail below, manages, tracks and records selected transactions involving the participating prescribers, pharmacies and patients.

To identify various pharmaceutical trial products, the system utilizes a medium, such as a magnetic card, which is encoded with specific information that particularly identifies a certain pharmaceutical trial product. Encoded media is then distributed to participating medical doctors or prescribers. Once the encoded product trial media is received by the prescribers, the prescribers then activate the selected product trial media. Activation is accomplished, in part at least, by utilizing a prescriber terminal to communicatively link the selected product trial media with the central computing station or host. Once the product trial media has been activated, the prescriber then transfers the activated product trial media to patients. The patients then present the activated product trial media to participating pharmacies. Prior to filling the prescriptive pharmaceutical trial product identified by the media, the pharmacy engages in a procedure designed to validate the patient-presented pharmaceutical trial media. To validate the presented product trial media, the pharmacy communicatively links the presented media to the central computing station via the pharmacy terminal. After making selected verifications, the central computing station validates the presented product trial media. Validation results in the pharmacy dispensing the pharmaceutical trial product identified by the presented media.

Prior to activation and validation, the system and method of the present invention requires that the participating pharmacies and prescribers establish "authorization", that is that they are in fact authorized participants in the pharmaceutical trial product distribution program.

After validation and dispensing, a database associated with the central computing station will have recorded the activation and validation transactions and other data related thereto. Based on the recorded data, audit and accounting procedures can follow. Particularly, dispensed pharmaceutical trial products can now be replaced at the pharmacy level, via wholesalers, by simply replenishing quantities of pharmaceutical products dispensed by the participating pharmacies. Replenishment of the pharmaceutical trial product can be carried out and managed in accordance with the records of the database. Moreover, it is contemplated that participating pharmacies will be remunerated with a dispensing fee that can be determined based on the records of the database associated with the central computing station.

It is therefore an object of the present invention to provide a more effective and efficient process for managing the distribution of pharmaceutical trial products.

Another object of the present invention is to provide a system and process for the distribution of pharmaceutical trial products that inherently includes "checks and balances" and which in the end is designed to ensure integrity and accountability throughout the entire process.

It is also an object of the present invention to provide a system and process for distributing pharmaceutical trial products that is more cost effective than conventional processes, especially processes that require special trial or sample packaging.

It is also an object of the present invention to provide a system and method for managing the distribution of pharmaceutical trial products that provides for the computerized recordation of selected transactions surrounding the prescription and distribution of pharmaceutical trial products.

Another object of the present invention is to provide an improved method of distributing pharmaceutical product samples that eliminates the need for pharmaceutical manufacturers to specially package drug product samples differently from normally packaged drugs, thereby cutting costs associated with manufacturing, storing, and distributing drug product samples.

A further object of the present invention is to provide an improved method of distributing drug product samples while maintaining the role of outside pharmaceutical sales representatives in promoting and marketing drug products.

Other objects and advantages of the present invention will become apparent and obvious from a study of the following description and the accompanying drawings, which are merely illustrative of such invention.

BRIEF DESCRIPTION OF THE DRAWINGS

FIG. 1 is a schematic illustration of the system of the present invention for managing the distribution of pharmaceutical trial products.

FIG. 2A is a front side view of the pharmaceutical trial product media that forms a part of the present invention.

FIG. 2B is a back side view of the pharmaceutical trial media.

FIG. 3A is a front side view of the authorization media that forms a part of the present invention.

FIG. 3B is a back side view of the authorization media.

DETAILED DESCRIPTION OF THE INVENTION

Figure 4A:
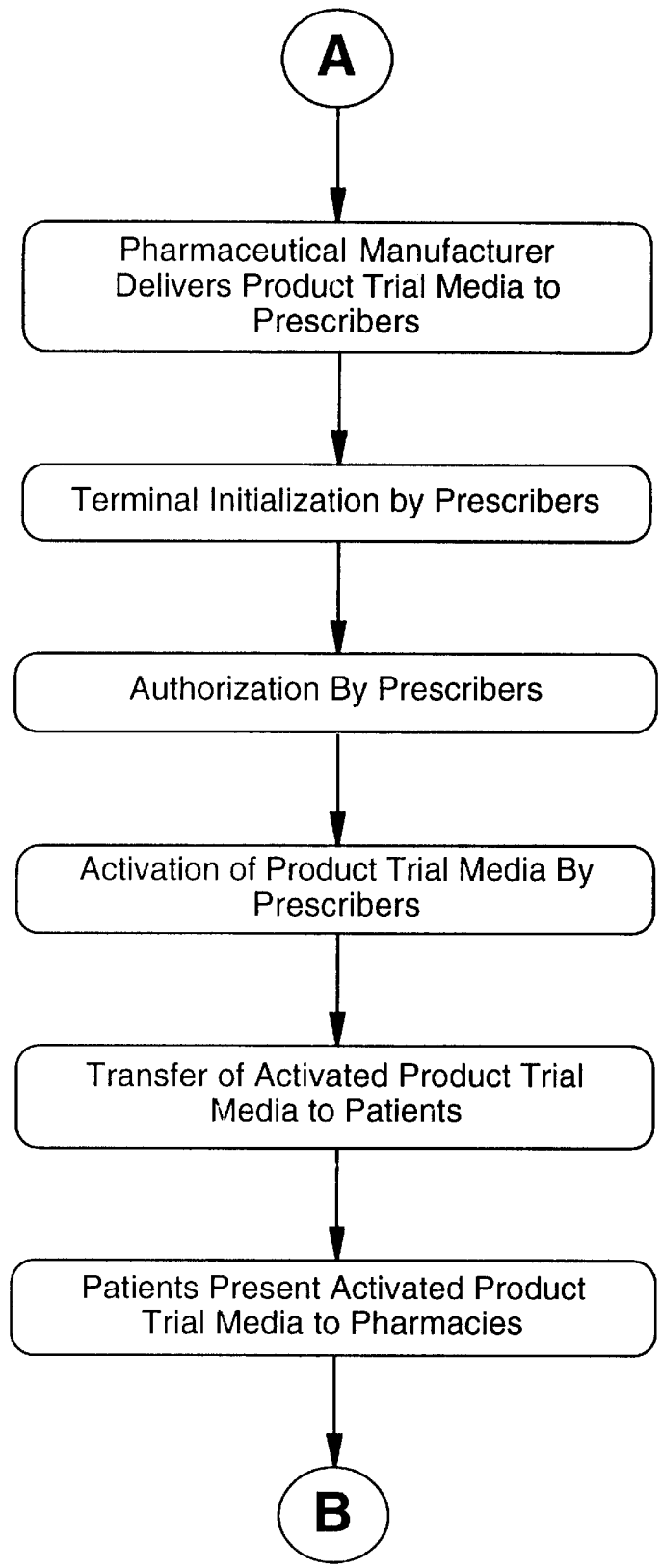
FIGS. 4A–4B depicts a flow chart that shows the basic steps entailed in distributing, tracking and managing pharmaceutical trial product distributed in accordance with the present invention.

With further reference to the drawings and particularly to FIG. 1, the system utilized for carrying out the present invention is shown therein and indicated generally by the numeral 10. System 10 includes a central computing station 12 that has associated therewith a database for storing data and information communicated to the central computing station 12 during various steps or phases of the pharmaceutical trial product distribution process. As will be appreciated from subsequent portions of this disclosure, the present invention contemplates the utilization of participating medical doctors or prescribers and pharmacies to effectuate the distribution of pharmaceutical trial products. In order to communicate with the central computing station 12, each participating prescriber and pharmacy is provided with a terminal communicatively linked with the central computing station 12. Therefore, it is appreciated that the system 10 of the present invention will include prescriber terminals 14 located at various participating prescriber sites and pharmacy terminals 16 located at various participating pharmacy sites. Both the prescriber terminals 14 and the pharmacy terminals 16 are capable of communicatively linking encoded media with the central computing station 12 where the encoded information associated with the media can be recorded in the associated database. Various types of communication terminals can be utilized at prescriber and pharmacy sites. However, as will be appreciated from subsequent portions of this disclosure, one such type of terminal is a conventional magnetic card reader that is adapted to accept magnetic cards and to read or interpret encoded information provided thereon and to communicate with the central computing station 12.

System 10 further includes what is referred to as a pharmaceutical product trial media that in FIG. 1 is indicated by the numeral 18. As will be appreciated from subsequent portions of the disclosure, the product trial media 18 identifies and is associated with a particular pharmaceutical trial product and is transferred and passed between participating prescribers, patients and pharmacies. The product trial media 18 is particularly encoded with pertinent information that identifies a particular pharmaceutical trial product and is designed to be compatible with the prescriber and pharmacy terminals 14 and 16. In particular, prescriber and pharmacy terminals 14 and 16 are capable of reading the product trial media 18 and communicating encoded information associated therewith to the central computing station 12 for processing and recordation.

Although the type and quantity of encoded information on the product trial media 18 can vary, it is contemplated that each individual product trial media 18 would be encoded with at least the following information:

a) media identification number;
 b) product identification number;
 c) product name;
 d) product form;
 e) product size;
 f) product quantity;
 g) media type;
 h) a series of manufacturer I.D. numbers;
 i) a date range In addition, as illustrated in FIGS. 2A and 2B, each individual product trial media 18 will have printed or embossed thereon certain identifying information such as:

a) pharmaceutical manufacturer's name;
 b) product name (trade name, generic name);
 c) product form;
 d) product size;
 e) product quantity;
 f) media identification number;
 g) prescriber, patient and pharmacy signature areas;
 h) prescriber and pharmacy approval code areas The product trial media 18 can assume various tangible forms. However, in the example illustrated in FIGS. 2A and 2B and discussed herein, the product trial media 18 is in the form of a conventional magnetic card which again is designed to be compatible with a READ-ONLY magnetic reader terminal located at prescriber and pharmacy sites.

Finally, the system 10 of the present invention includes authorizing media indicated by the numeral 20 that is distributed to participating prescribers and pharmacies. As with the product trial media 18, the authorizing media 20 can be in various tangible forms and in the example illustrated herein, the authorizing media assumes a READ-ONLY magnetic card form that is compatible with the prescriber and pharmacy terminals 14 and 16. Each individual authorizing media specifically identifies a participating prescriber or pharmacy. In the case of prescriber authorizing media, the same would be encoded with various identifying information such as:

a) the prescriber's name,
 b) prescriber's medical identification number,
 c) prescriber's control I.D. number,
 d) prescriber location identification.

In the case of pharmacy authorizing media, the same would include encoded information specific to and identifying a particular participating pharmacy. The encoded information on such a pharmacy authorizing media would include identifying information such as:

a) pharmacy name,
 b) name of individual pharmacists associated with the identified pharmacy,
 c) pharmacy control identification number, and
 d) pharmacy location identifier.

Also, as illustrated in FIGS. 3A and FIGS. 3B, the authorization media 20 includes printed or embossed information thereon such as prescriber or pharmacy I.D. number, pharmacy or prescriber name, card expiration date, and space for the signature of a physician or pharmacist.

Figure 4B:
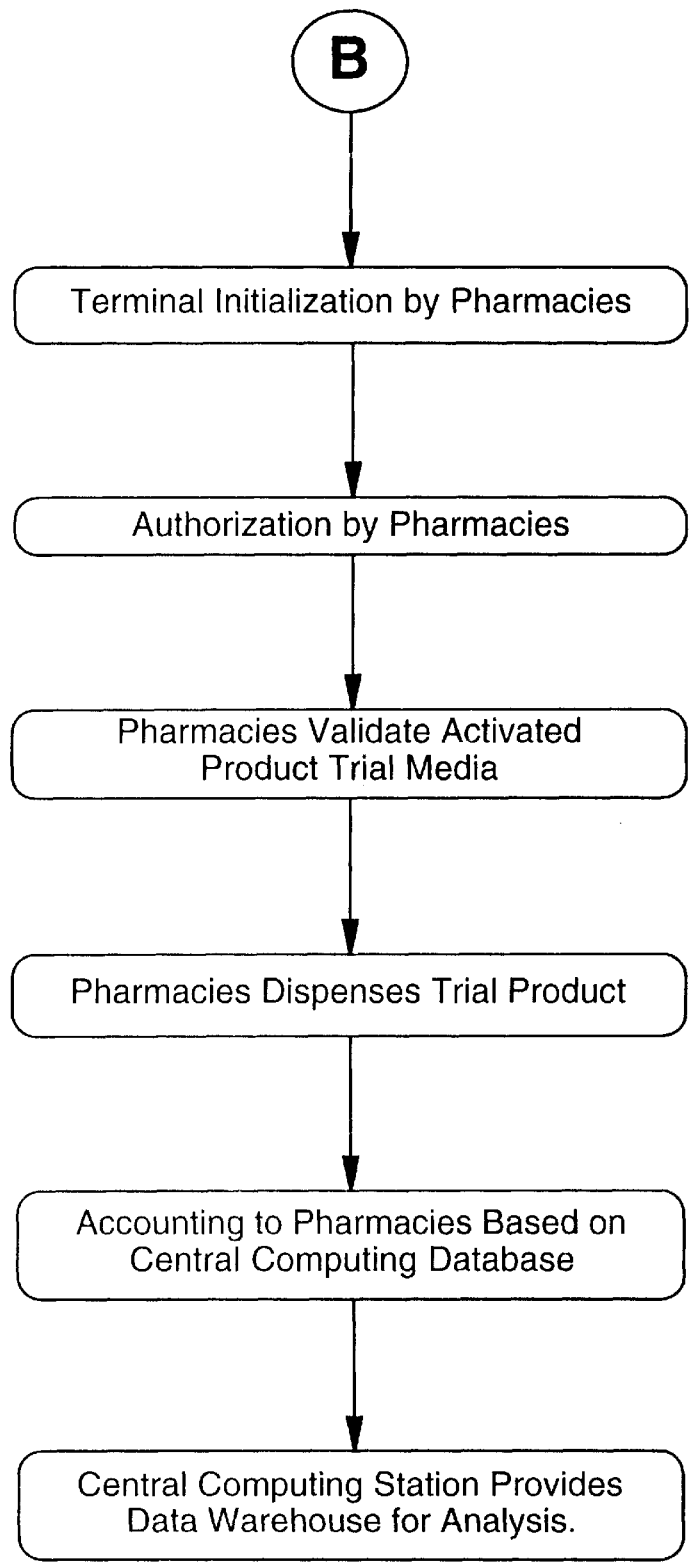

As will be discussed in more detail later, the authorizing media 20 is compatible with the prescriber and pharmacy terminals 14 and 16 and consequently, encoded identifying information associated with the individual authorizing media 20 can be reviewed and verified by the central computing station 12 prior to the participating prescribers and pharmacies having access to the central computing station. The authorizing media 20 enables the system and the central computing station 12 in particular to verify that prescribers and pharmacies attempting to enter the system and network are in fact authorized to do so and are in fact authorized participants in the pharmaceutical trial product distribution program of the present invention. See FIGS. 4A–4B.

The present invention entails a pharmaceutical trial product distribution method or process where pharmaceutical trial products are actually prescribed by a participating medical doctor or prescriber and not directly delivered to the patient by the prescriber as is conventional practice today. Once the pharmaceutical trial product has been prescribed, the patient then proceeds to a participating pharmacy where the prescription for the trial or sample pharmaceutical product is filled. Prescriber and pharmacy transactions are all monitored and recorded by the central computing station 12. Periodically, the participating pharmacies are compensated for the trial product dispensed and the services performed. Compensation would typically include replenishment of dispensed trial product through a wholesaler plus a dispensing fee, all of which is established by recorded transactions within the central database.

It is contemplated that the present system and method for distributing pharmaceutical trial products would be managed by an independent entity referred to as a program manager and that a number of pharmaceutical manufacturers would join together in a consordium or the like to participate in the pharmaceutical trial product distribution program, all of which would be administered and managed by the program manager. However, it is to be appreciated that the present pharmaceutical trial product distribution system and method can be carried out in other forms including a program administered and managed totally by a single pharmaceutical manufacturer.

In developing and implementing the pharmaceutical trial product distribution program of the present invention, participating prescribers and pharmacies must be established. In this regard, it is contemplated that the program manager in cooperation with participating pharmaceutical manufacturers or suppliers, sometimes referred to as pharmaceutical members, ientify certain prescribers and pharmacies that are authorized to participate in the program. Thereafter, the program manager issues specific authorizing media 20 to each of the prescribers and pharmacies authorized to participate in the program. Note that each authorizing media 20 is specifically encoded to identify a certain prescriber or pharmacy as well as the physical location or locations of that prescriber or pharmacy. In addition to the authorization media 20, prescriber terminals 14 and pharmacy terminals 16 are also delivered to the participating prescribers and pharmacies.

The prescriber and pharmacy terminals 14 and 16 are transaction-based communication units provided with both an EPROM chip and random access memory (RAM) for application operation. Each terminal is electrically powered and adapted to communicate with the central computing station or host 12 through a conventional telephone system. A user keypad having both function keys and a ten-number keypad are incorporated into each terminal. Application, prompt and approval instructions are communicated through an LED display that forms a part of each terminal.

The EPROM chip of each terminal is provided with a series of data fields that are used in a terminal initialization procedure that is designed to verify that a respective terminal is properly located physically and is under the control of an authorized and participating prescriber or pharmacy. In the way of example, the data fields of the EPROM chip could include: terminal serial number, prescriber or pharmacy identification, location or locations (physical address) for the participating prescriber or pharmacy assigned to that terminal, and location fax and telephone number. In addition, the EPROM chip of each terminal would include a check digit/analog code matrix used in establishing the authenticity of the terminal.

Now, turning to the RAM of the respective terminals, it is appreciated that the capacity of the RAM may vary but it is contemplated a storage capacity of 32K bytes would be sufficient to handle downloaded application programming from the central computing station 12. Data fields for the RAM may include a series of server (central computer station) phone numbers, a check digit/analog code index field, check digit/analog code multiplier-divisor, check digit/analog answerer, check digit/analog code formula, and system date and time.

The above discussion deals generally with the basic prescriber and pharmacy terminals 14 and 16 that are contemplated to be used in carrying out the pharmaceutical trial product distribution method and program of the present invention. Details of the construction and programming of the terminals are not dealt with herein because such is not per se material to the present invention and further, because such terminal designs are well appreciated by those skilled in the art and are in fact commercially available. While various types of terminals may be employed by participating prescribers and pharmacies, it is contemplated that a terminal design of a conventional magnetic card reader would be efficient and cost effective for the present pharmaceutical trial product distribution program.

Initially, various pharmaceutical members distribute individual product trial media 18 to participating medical doctors or prescribers. This distribution can be carried out by sales representatives of the pharmaceutical members. At the same time, the program manager (administrator of the pharmaceutical trial product distribution program) may distribute both terminals and authorizing media 20 to both participating medical doctors and pharmacies. It is appreciated that prior to the initiation of the program and in fact on an ongoing basis, the database associated with the central computing station 12 is loaded with data corresponding to the distributed product trial media 18 and authorization media 20 as well as data that identifies each individual terminal to be delivered to participating prescribers and pharmacies. Such is important in carrying out the various integrity checks that will form a part of the pharmaceutical trial product distribution program of the present invention.

Figure 5:
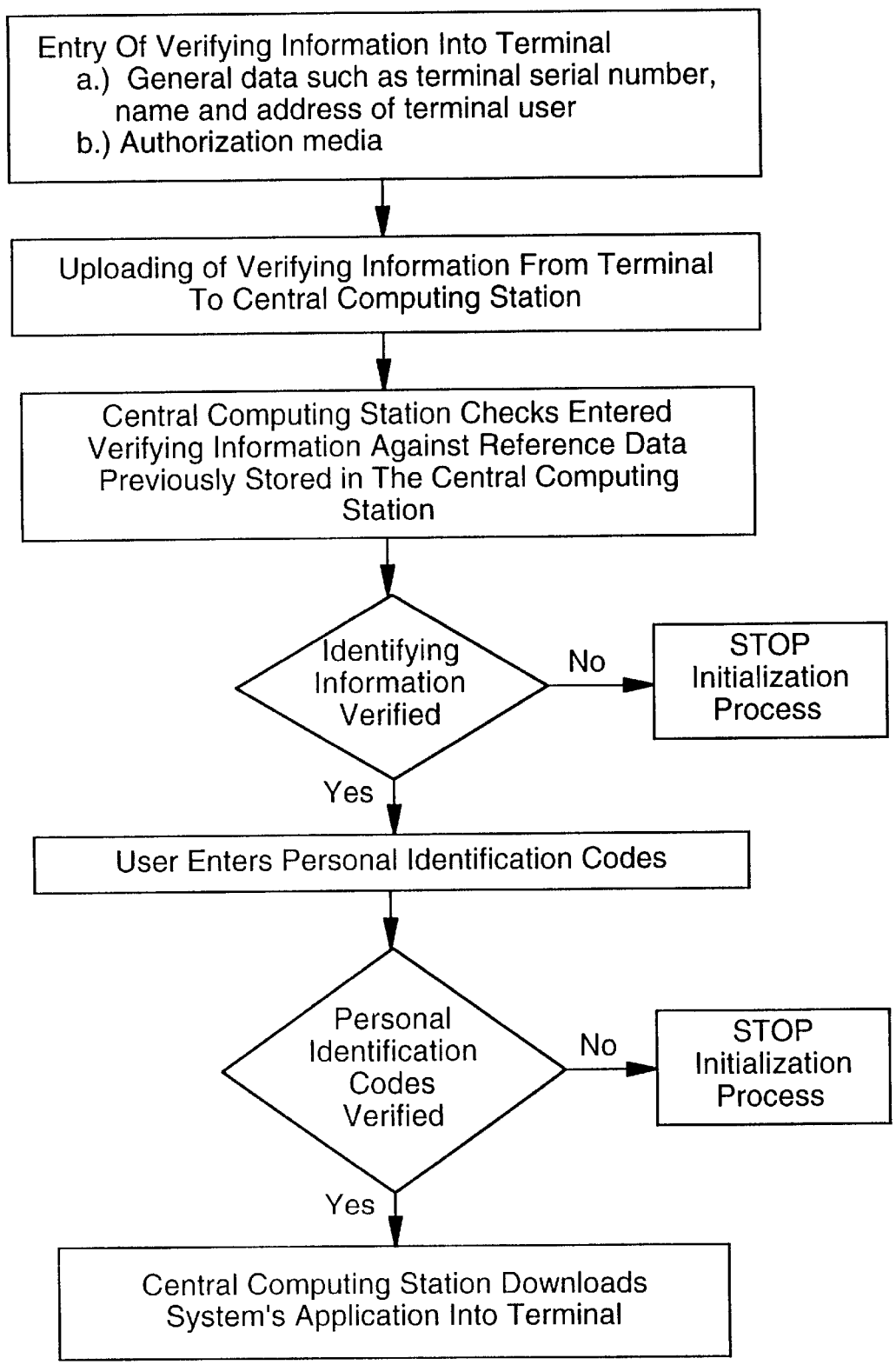
FIG. 5 is a flow chart that depicts the basic steps entailed in terminal initialization, whether it be at the prescriber or pharmacy level.
Figure 6A:
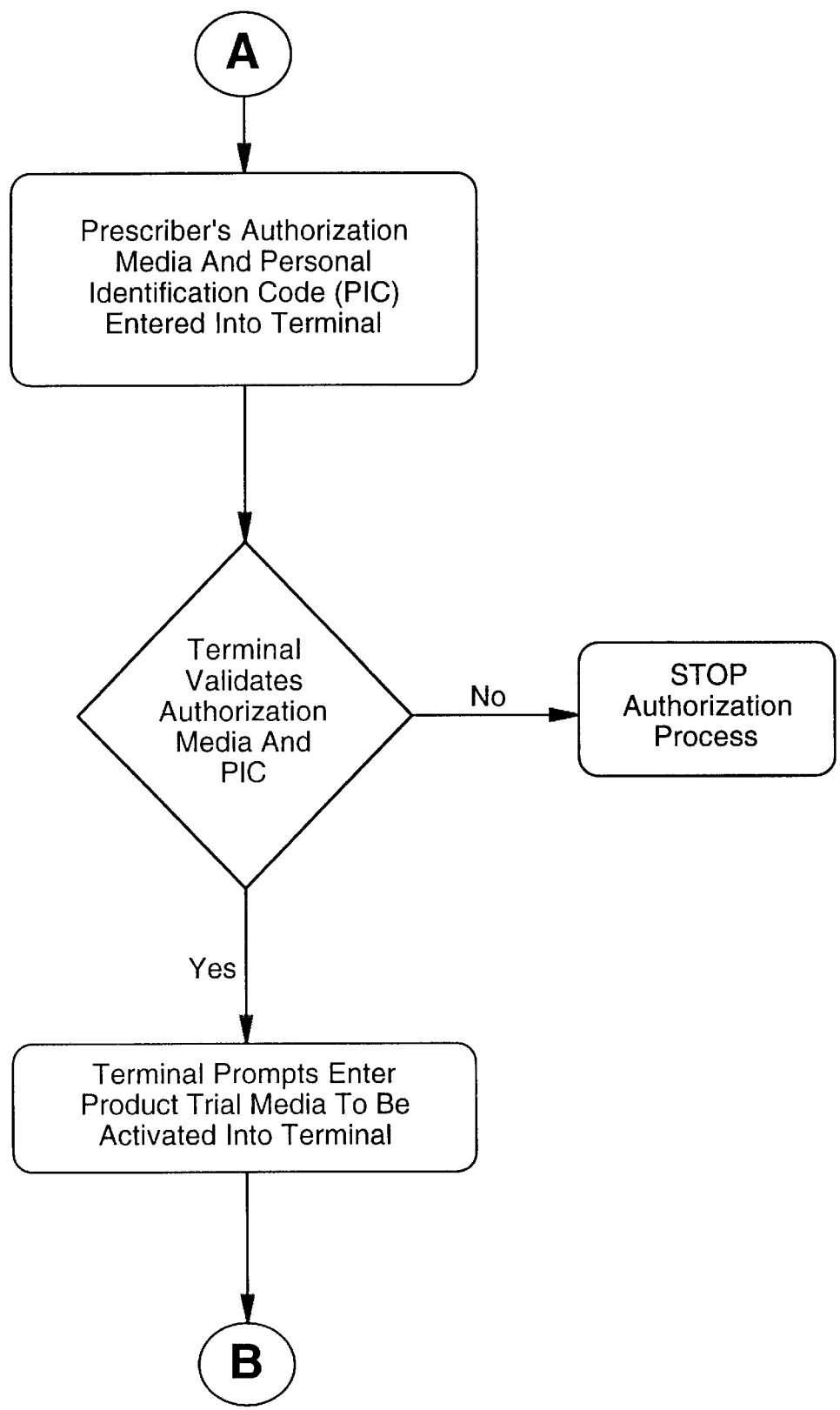
FIGS. 6A–6D depicts a flow chart that shows the basic steps involved in the prescribers activating pharmaceutical trial media.
Figure 6B:
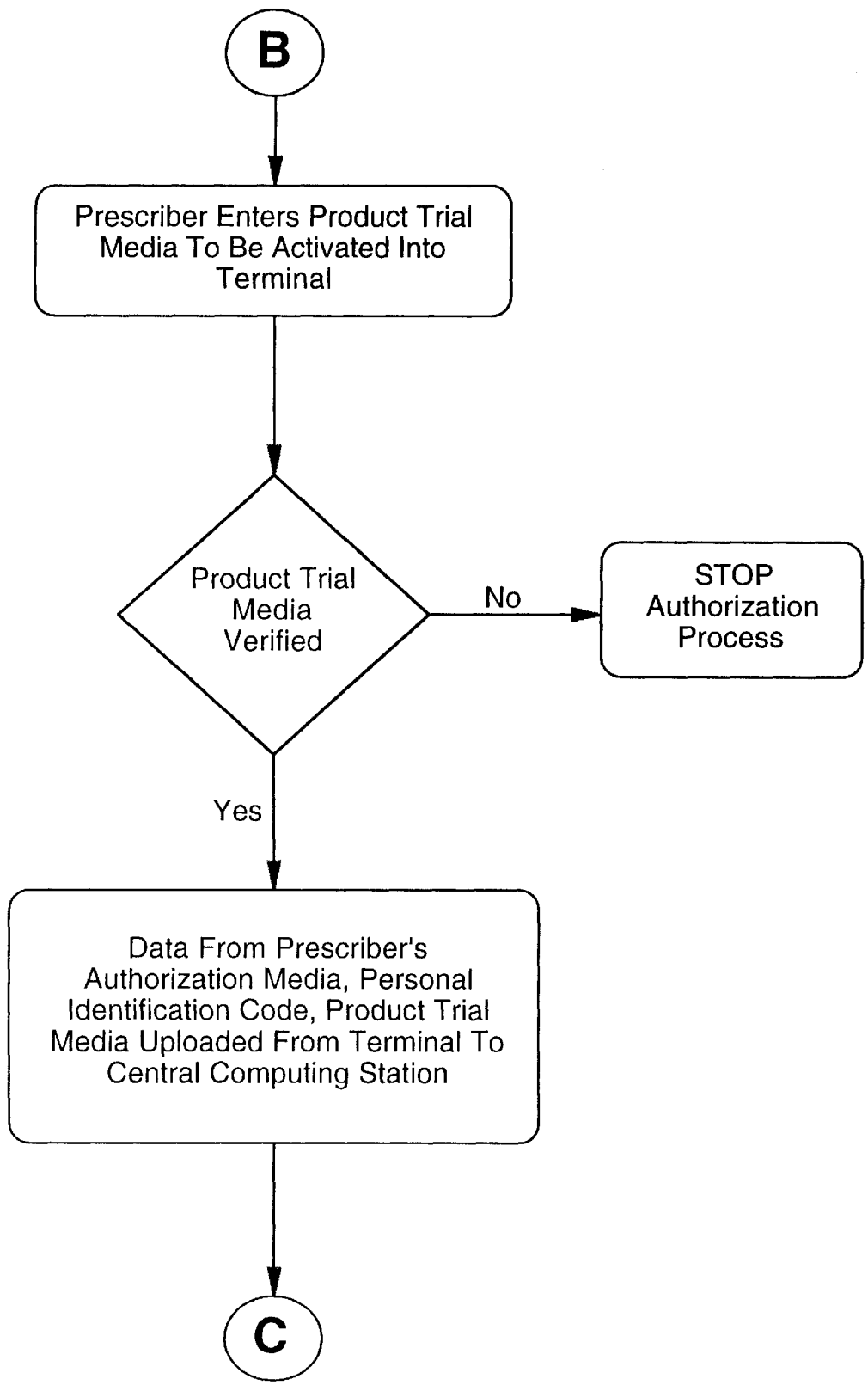
Figure 6C:
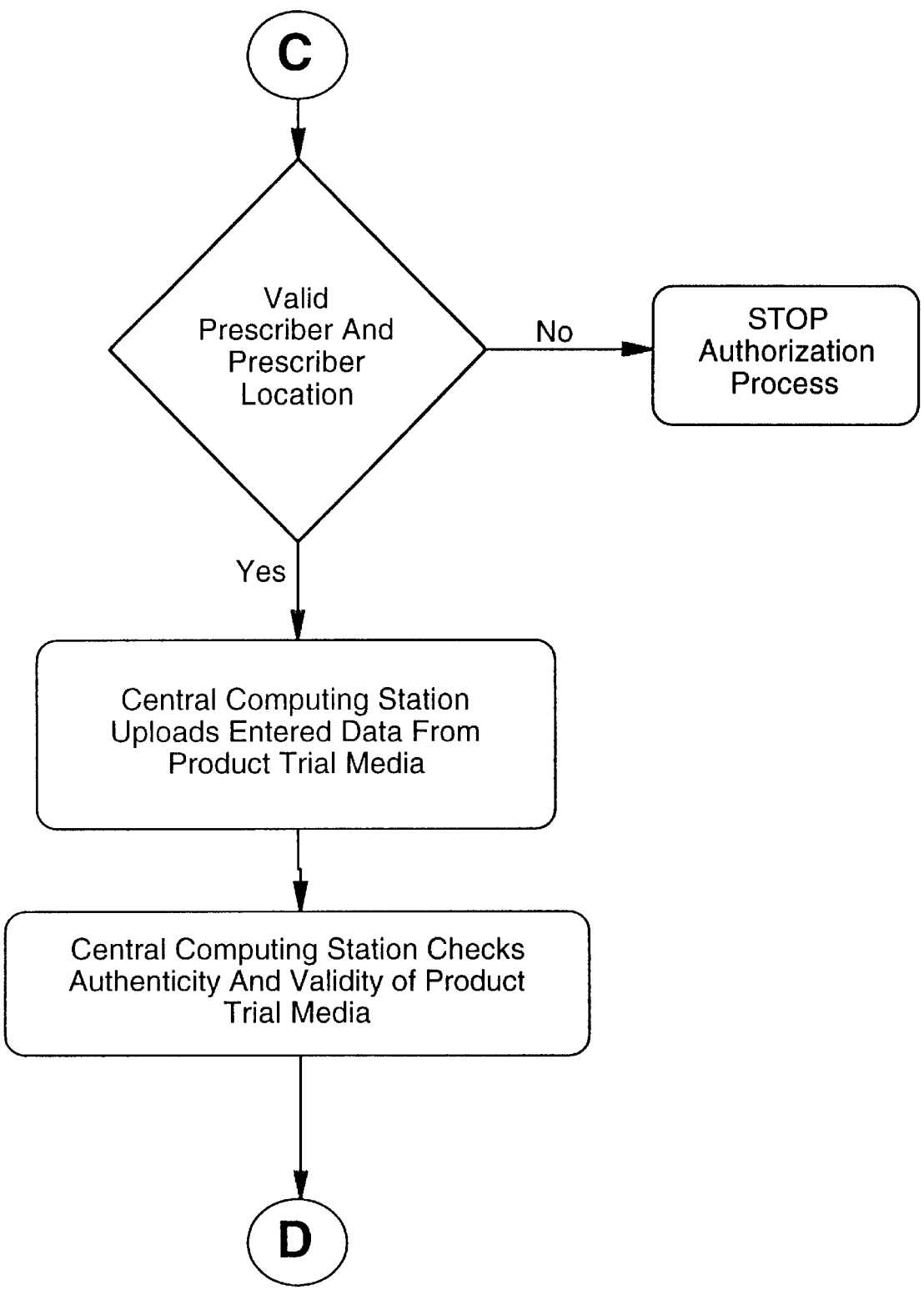
Figure 6D:
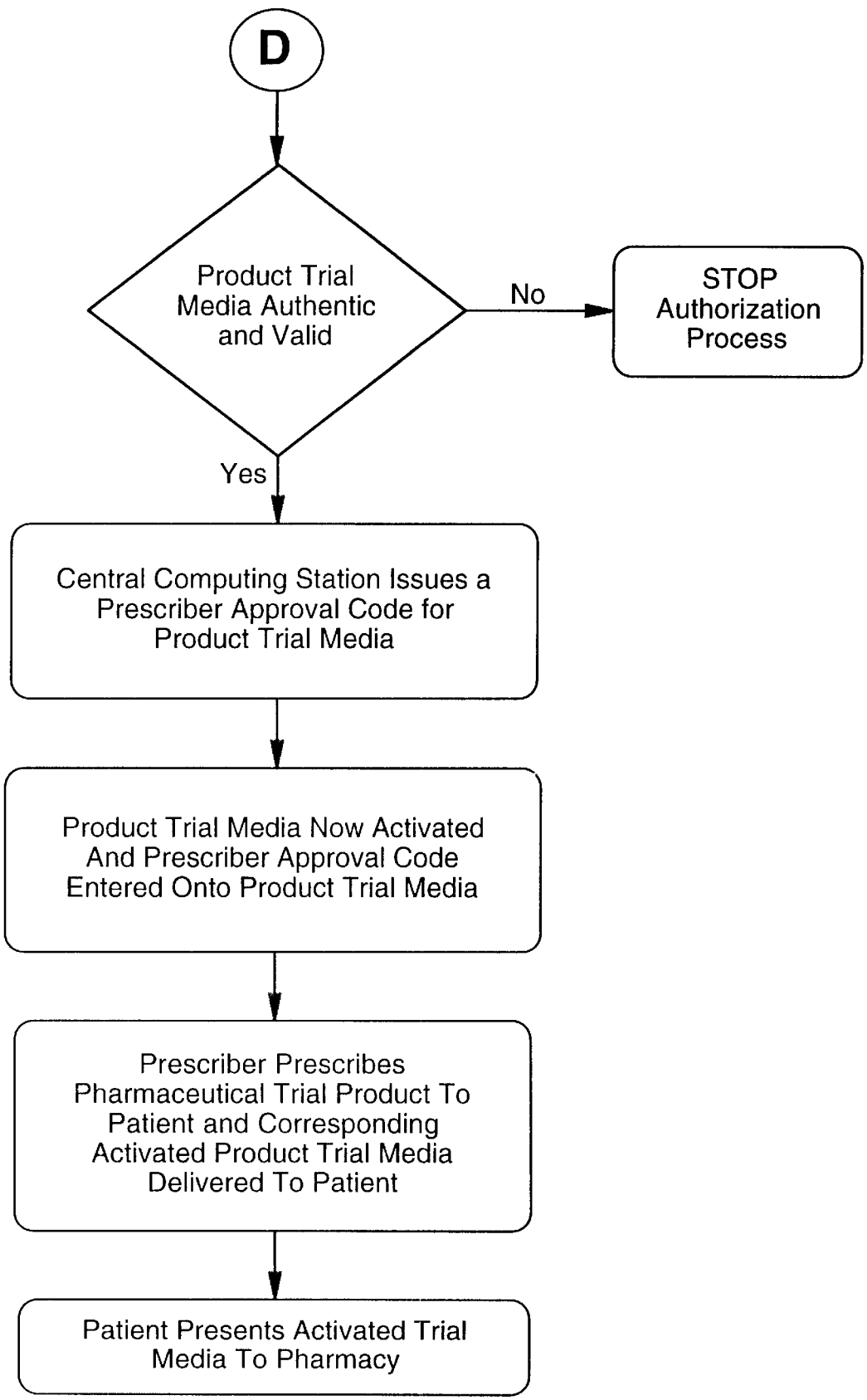

Prior to entering the system and participating in the pharmaceutical distribution program, each participating prescriber and pharmacy must proceed through a terminal initialization process. This terminal initialization process, as illustrated in FIG. 5, is designed to discover and identify unauthorized participants and to generally prevent unauthorized use of the system.

To initialize a terminal, the prescriber or pharmacy connects the terminal to an AC power outlet and a conventional phone line. Once the terminal is placed in an "on" state, the prescriber or pharmacy presses a "setup" function key. The terminal then automatically responds and requests information pertinent to the data fields of the EPROM chip. In the way of examples, the terminal requests the user to input into the issued terminal the terminal serial number, practice name or pharmacy operating from the location of the terminal, the physical address of the location of the terminal, location communication telephone number, location business telephone number and location fax number.

Next, and still as a part of the terminal initialization process, the terminal requests that the prescriber or pharmacy user enter its issued authorization media 20. In the case of a magnetic card media and reader, the prescriber or pharmacy simply swipes its authorization media card 20 through a magnetic card reader and encoded data on the authorization media card 20 is recorded in the RAM of the terminal.

Thereafter, the terminal automatically dials and connects to a terminal initialization service that forms a part of the central computing station 12. The initialization service then uploads all data from the terminal into the database of the central computing station 12 including data recorded on the EPROM chip and information previously encoded on the authorization media 20 and now stored in the RAM of the terminal.

Based on independently entered reference data previously entered into the database of the central computing station, the data uploaded from the terminal during this initialization process can be checked against the reference data already stored in the database of the central computing station. At this point, the central computing station can verify whether a certain serial number terminal is properly coupled with a certain physical location and with a certain prescriber or pharmacy. If all relevant data uploaded from the terminal does not correspond to the reference data then the initialization process is failed and access to the system and program is denied.

In the specific initialization method being discussed herein, the above does not complete the total initialization process. After passing the above, the individual prescriber or pharmacy is requested to enter a personal identification code, commonly referred to as a PIN. The personal identification code is furnished confidentially to the participating prescribers and pharmacies through the program manager and can be permanent or temporary. If temporary, the user will be subsequently requested to enter a personally devised code which becomes the user's permanent identification or PIN code. In any event, after the central computing station has requested entry of the user's personal identification code, the participating prescriber or pharmacy then enters the personal identification code into the system database and the central computing station then verifies the personal identification code and cross-checks the same with respect to uploaded terminal data, that is, data found on the EPROM chip and the terminal's RAM. If the personal identification code entered is determined to be an invalid personal identification code for any reason, the prescriber or pharmacy is denied access to the system. On the other hand, if the personal identification code is deemed to be valid then the central computing station indicates on the terminal's display "downloading application". At this time, the system's application is then downloaded into the terminal's RAM storage. Thereafter, the terminal displays "download complete" and this completes the terminal initialization process. The initialized terminal is then ready to be used on a periodic basis in the pharmaceutical trial distribution program of the present invention. Not that this same initialization process is carried out for both participating prescribers and pharmacies.

The product trial media 18 delivered to the participating prescribers arrive in an unactivated state. That is, the product trial media in an unactivated state cannot be validated by a participating pharmacy and accordingly, pharmaceutical trial product identified by that media cannot be dispensed. In the method of distributing pharmaceutical trial product of the present invention, the participating prescribers actually activate the product trial media through a procedure where the product trial media is communicatively linked with the central computing station or host 12 via a prescriber's terminal. See FIGS. 6A–6D which show a flow chart that depicts the basic steps involved in the activation process. However, before any unactivated product trial media can be activated by a prescriber, the prescriber must establish authorization. This can be carried out in a variety ways. In one embodiment of the present invention, activation of product trial media 18 is conditioned first upon the prescriber evidencing a valid authorization media. This is accomplished by the prescriber's terminal reading the prescriber's authorization media 20. Encoded information associated with the prescriber's authorization media 20 is recorded within the RAM of the prescriber's terminal. In particular, the terminal records the prescriber's identification number associated with the prescriber's authorization media 20. At that point, the terminal requests the prescriber to enter the prescriber's personal identification code. Next, the terminal requests the prescriber to enter the quantity (number) of pharmaceutical trial media that the prescriber desires to activate. Thereafter, the prescriber enters into the keyboard of the prescriber terminal the numeric quantity of product trial media 18 to be activated by the system. The prescriber terminal then prompts the prescriber to communicatively link the product trial media to be activated with the prescriber's terminal. In cases where the product trial media 18 assumes the form of magnetic cards for example, the prescriber simply swipes the product trial cards to be activated through a card reader-type terminal. One by one, the prescriber swipes the product trial media to be authorized through the prescriber's terminal.

As each product trial media is read by the prescriber's terminal, an authenticity check is made by the terminal. Specifically, the prescriber's terminal authenticates each product trial media read into the terminal. While various forms of authentication can be performed, in the present method, authenticity is established by the prescriber's terminal checking the product trial media I.D. and verifying that a valid answer results from the various check digit/analog code fields stored in the terminal. If the product trial media is deemed authentic, then the prescriber's unit then displays "product trial media valid". If the prescriber terminal determines that the product trial media is not valid, the terminal indicates such and the product trial media is not activated.

Once the prescriber has completed the activation of a certain number of product trial media the prescriber terminal dials a central computing station 12. At this point, the prescriber terminal uploads stored information corresponding to the prescriber authorization media and the prescriber identification code to the central computing station 12. The central computing station 12 validates the prescriber authorization media and the personal identification code. Once this validation has been established the central computing station uploads all of the product trial media information previously read into the prescriber's terminal during the present activation procedure. It is at this time that the central computing station 12 approves the "activation" of the entered product trial media and issues a specific approval code to the prescriber. The prescriber then records the prescriber approval code onto the face of the respective individual product trial media just activated. Once certain product trial media 18 has been activated, the central computing station 12 denotes in its associated database that certain product trial media 18 has been activated, the activation date, and the identity of the prescriber activating the product trial media. The prescriber then appropriately stores the activated product trial media 18.

To dispense the pharmaceutical trial product represented by the activated product trial media, the prescriber signs the product trial media and delivers the same to a participating patient. The patient in turn presents the activated product trial media to a participating pharmacy for the purpose of filling the trial product prescription of the prescriber.

Prior to actually filling the pharmaceutical trial prescription, the participating pharmacy, like the prescriber, must establish authorization. First, like the prescriber, the pharmacy terminal is subjected to the initialization test discussed above. This basically establishes that the issued terminal to the participating pharmacy is in fact the correct terminal, is properly physically located, and is associated with the assigned pharmacy. Again, this initialization procedure, as discussed above, is not contemplated to be a daily procedure but is only a basic initialization step for the participant utilizing the terminal and the system.

Figure 7A:
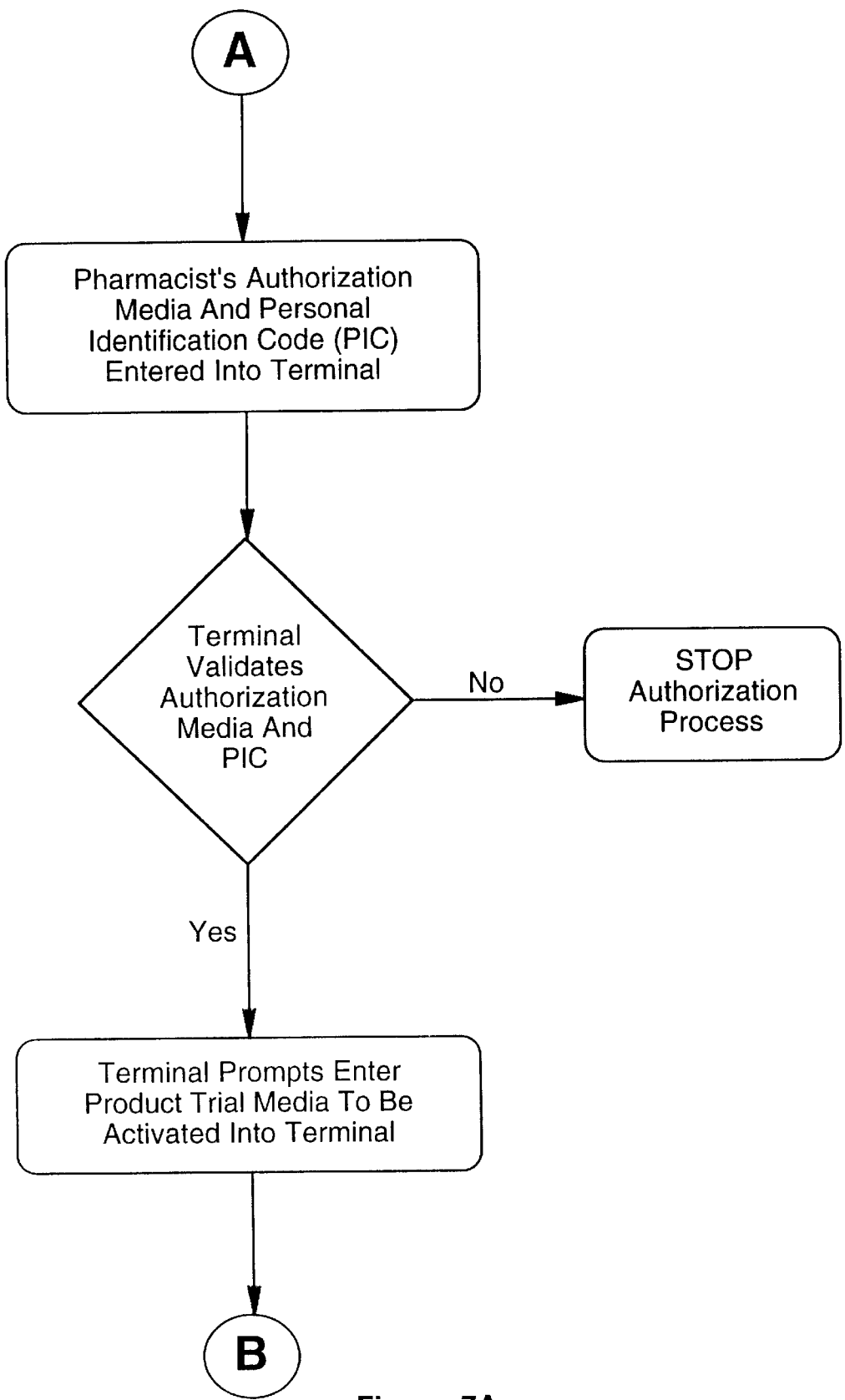
FIGS. 7A–7E depicts a flow chart that shows the basic steps involved in validating activated product trial media and dispensing pharmaceutical trial products in response to the validation of product trial media.
Figure 7B:
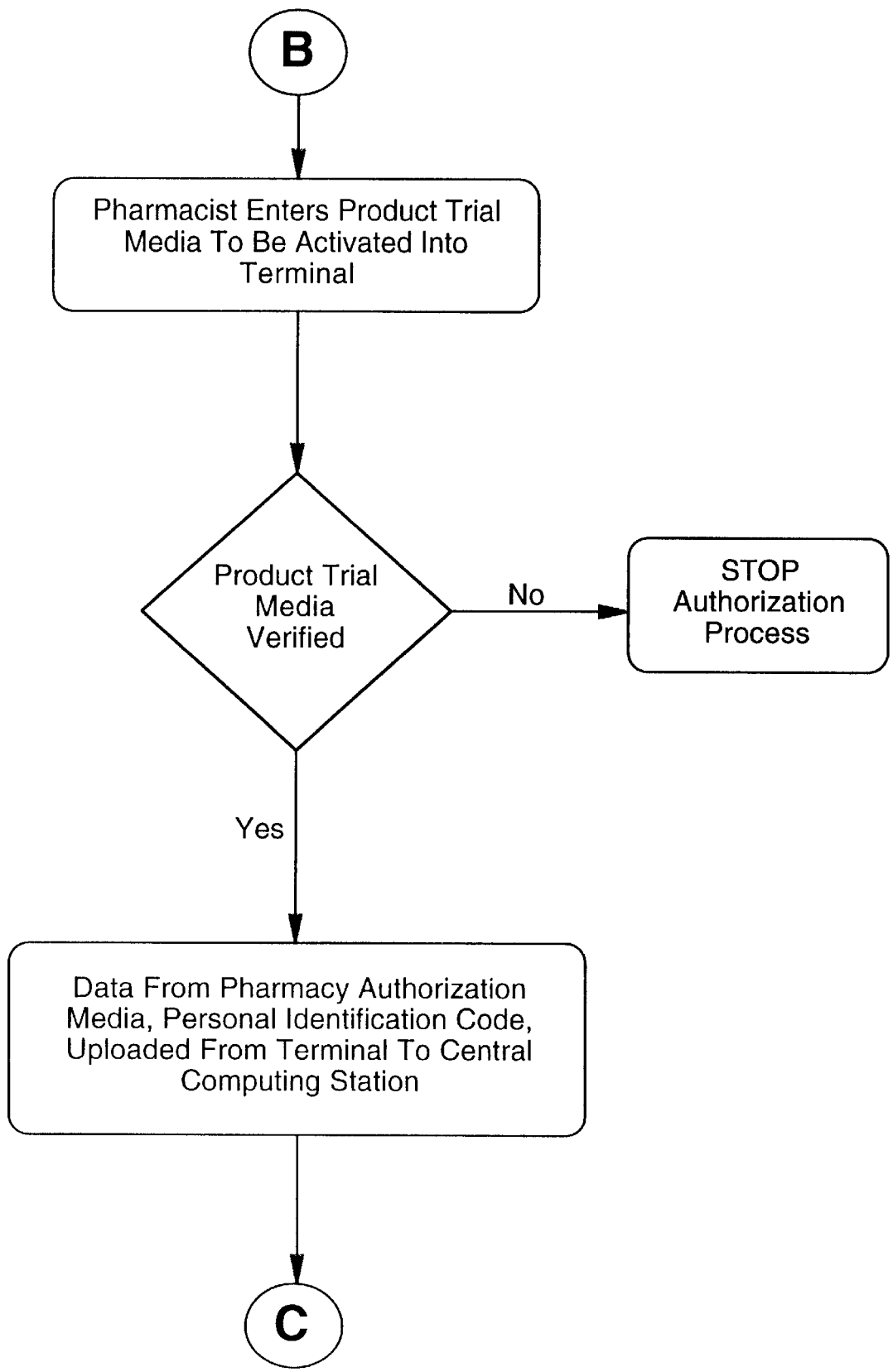
Figure 7C:
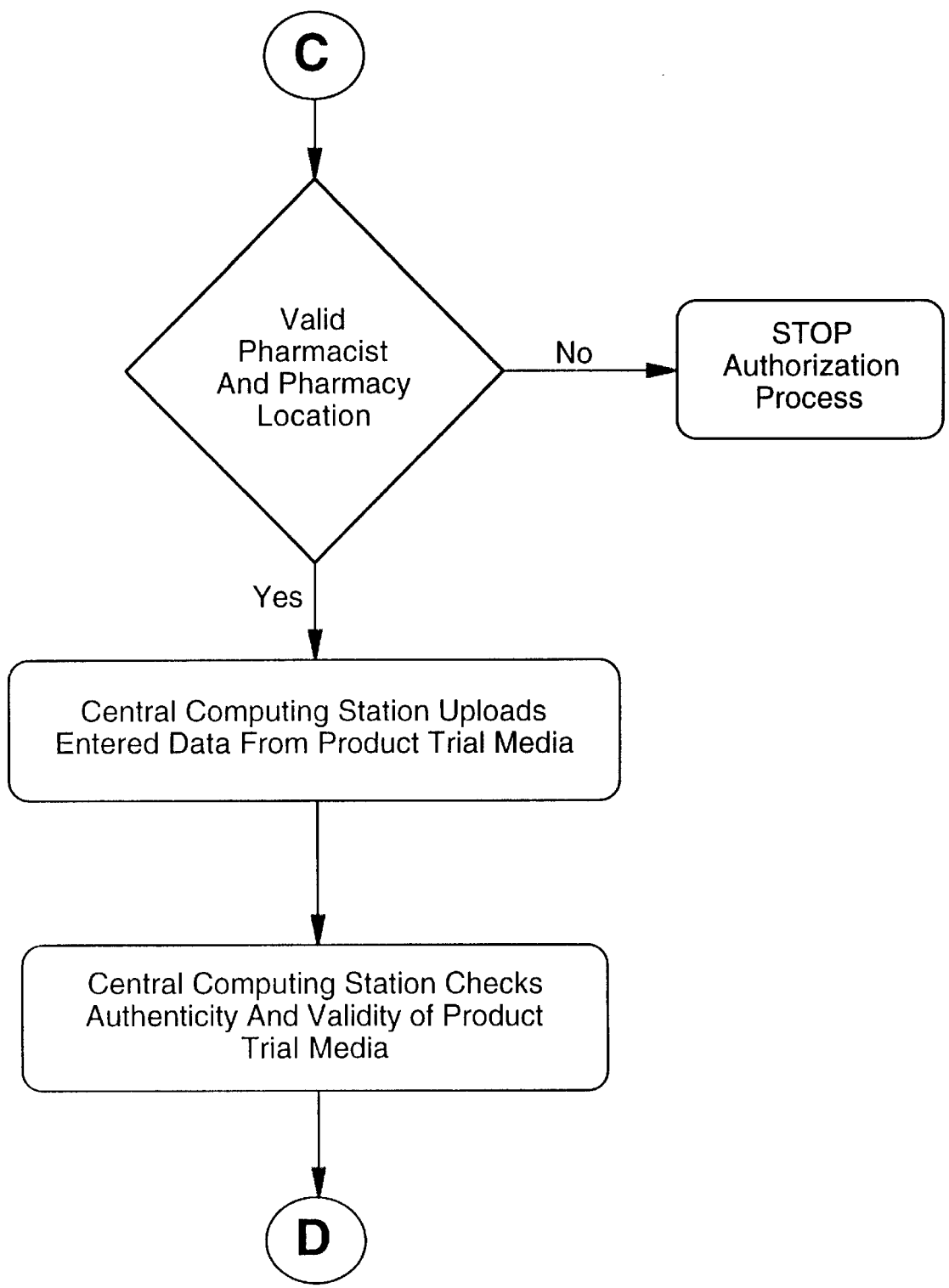
Figure 7D:
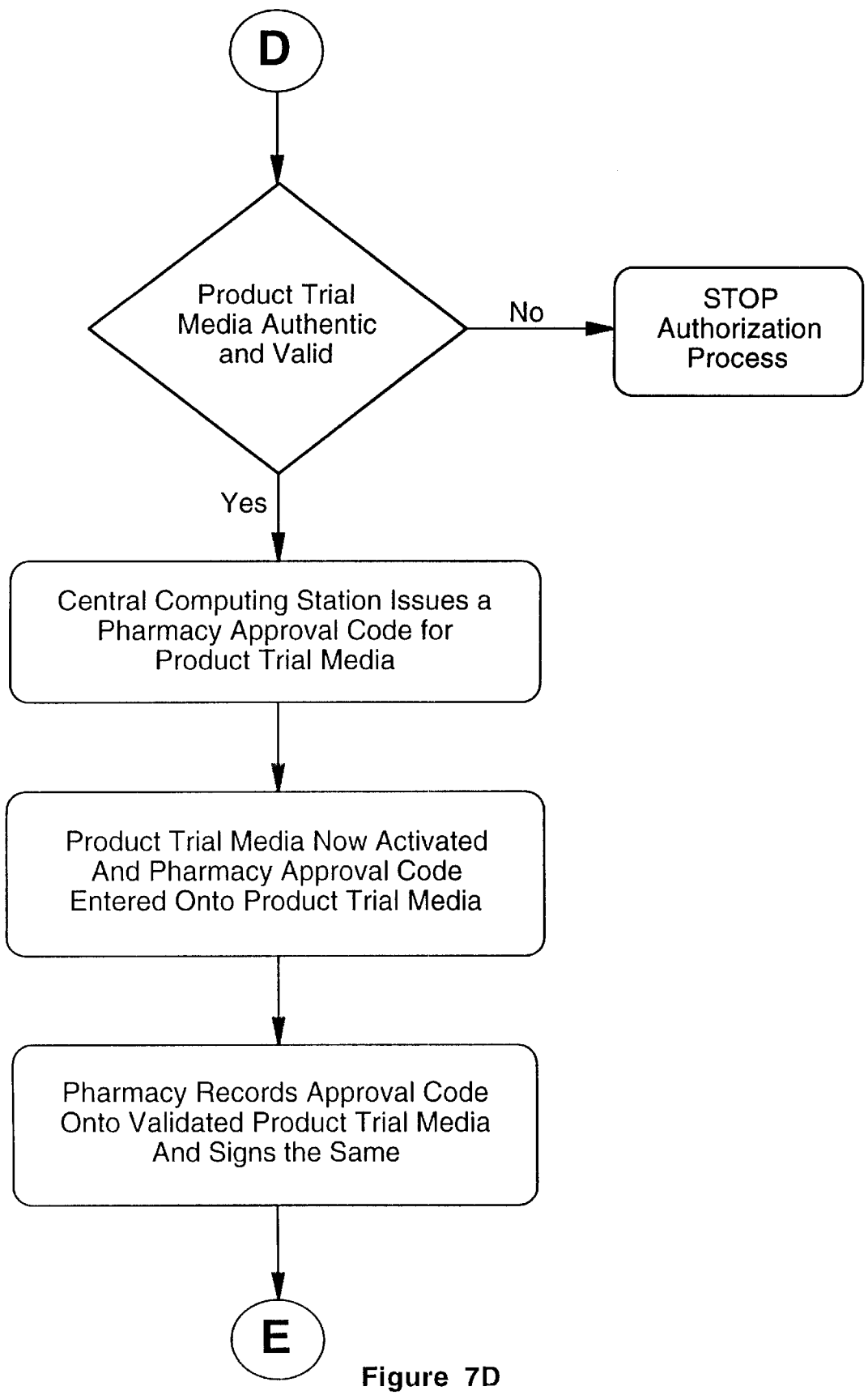
Figure 7E:
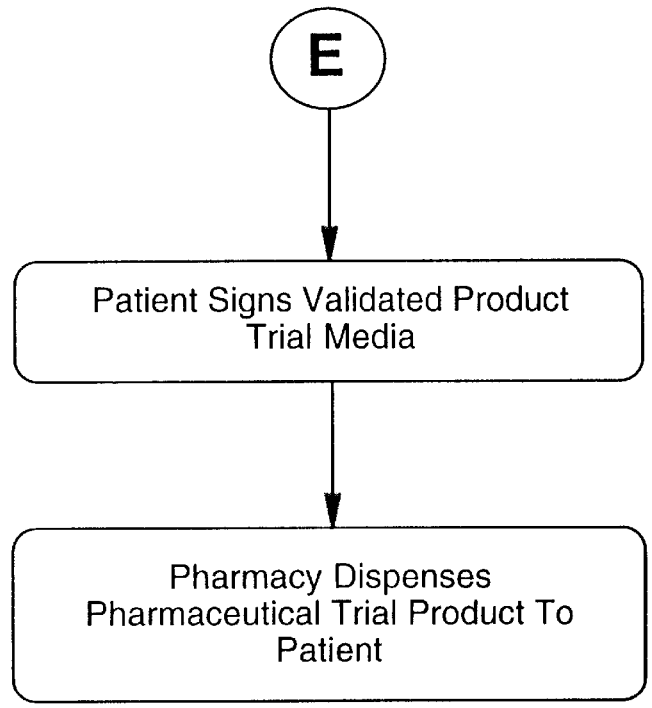

However, before the pharmacy can fill the prescriptive trial product of any presented product trial media 18, the product trial media must be subjected to a "validation" procedure. The "validation" procedure is basically illustrated in FIGS. 7A–7B. Essentially, this validation procedure establishes that the presented product trial media 18 is authentic, still within an acceptable date range, has been activated by a prescriber, and has not previously been validated. Once validation is established for any presented product trial media, then the participating pharmacy can issue the prescriptive trial pharmaceutical product to the patient.

Details of the validation process will not be dealt with here in great detail because pharmaceutical "validation" of product trial media parallels prescriber "activation" of the product trial media just described. That is, "validation" by the participating pharmacy entails steps and procedures that are similar in function and result as the steps and procedures engaged in by the prescriber in activating certain product trial media. But briefly, the validation step entails the participating pharmacy establishing authorization. This can be carried out in a variety of ways. However, in the process contemplated herein, the participating pharmacy would communicatively connect its authorization media 20 with the pharmacy terminal and after establishing a valid authorization media the participating pharmacy would enter its personal identification code. Thereafter, the terminal prompts the pharmacy to read the presented product trial media 18 into the terminal. As an individual product trial media is read into the pharmacist's terminal, the terminal first checks for complete authenticity of the presented product trial media 18. Like with the prescriber, the identification of the media is checked, the date range of the media is checked and the terminal seeks a valid answer from the check digit/analog code fields. If authenticity is not established, it follows that the participating pharmacy cannot dispense corresponding pharmaceutical product. However, if authenticity is established then the pharmacies' terminal dials the central computing station and data and information from the pharmacies' authorization media and personal identification is uploaded to the database of the central computing station 12. The central computing station establishes that the uploaded information is valid and then information from the pharmacies' terminal related to the presented product trial media 18 is uploaded to the central computing station. Assuming full validation, the central computing station issues a pharmacy approval code and the pharmacy records that approval code on the actual presented product trial media 18. In addition, both the pharmacy and the patient sign the now validated product trial media 18. Once validation is established the pharmacy then dispenses pharmaceutical trial product authorized by that valid product trial media and permanently stores the validated media. At the same time, the central computing station 12 records the full validation data within its database by showing that a particular product trial media 18 has been validated, the date of such validation, and the identity of the pharmacy validating the same.

Obviously, the database associated with the central computing station 12 will possess a full record of all transactions of the program including activations and validations. Importantly, the recorded transactions reveal the dispensing activities of each participating pharmacy. This serves as a basis for replenishing to the participating pharmacy pharmaceutical products dispensed in the present program and for the payment of dispensing these to the participating pharmacies. Typically, the pharmaceutical trial product to be replenished can be replenished through wholesalers that serve the participating pharmacies.

A wealth of data can be discerned from the central computing database. For particular pharmaceutical members, data representing the identity of product and the quantity of a particular trial product prescribed and dispensed over a selected period of time is obviously readily available. More detailed data and records representing the specific activities of particular prescribers or pharmacies is also available. In the end, a wide variety of reports can be generated from the database. These reports can be so extensive and so detailed that the participating pharmaceutical members can study and evaluate "cause and effect" based on the recorded data.

In summary, the present method of tracking and managing the dispensing of pharmaceutical trial products centers around the utilization of a group of authorized prescribers and pharmacies and a centralized computing station that is specifically linked to the participating prescribers and pharmacies. Product trial media capable of being exchanged at a pharmacy for pharmaceutical trial product is delivered in an unactivated state to participating prescribers. After establishing authorization, the prescriber through a remote terminal and the central computing station "activates" certain product trial media. Once activated, the product trial media is capable of being prescribed or exchanged for a pharmaceutical trial product at a participating pharmacy site. The activated pharmaceutical trial media 18 is then delivered to a patient and the patient in turn presents the same to a participating pharmacy. The pharmacy must establish authorization to participate in the system and thereafter the presented activated product trial media is authenticated by the central computing station and is deemed valid. Next, the pharmacy dispenses the pharmaceutical trial product identified by that media. Thereafter, an audit and accounting function is performed based on the database associated with the central computing station. Accordingly, participating pharmacies can be compensated for the actual dispensed pharmaceutical product and for dispensing services performed.

The present method and program has been described as being carried out by utilizing magnetic cards and magnetic terminal readers. However, it is appreciated that other media forms and terminals could be utilized to carry out the basic method of tracking and managing the distribution of pharmaceutical trial products.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of dispensing, tracking and managing pharmaceutical trial products utilizing prescribers, pharmacies, and a central computing station, comprising the steps of:

a) forming a series of product trial cards by encoding on respective product trial cards information that identifies a particular pharmaceutical trial product;

b) issuing the product trial cards to participating prescribers;

c) activating the product trial cards after issuance to prescribers by the prescribers communicatively linking the product trial cards to the central computing station and wherein activation is established by the central computing station verifying the authenticity of the product trial cards, recording selected information encoded on the product trial cards in a database associated with the central computing station, and finally approving activation;

d) transferring a respective activated product trial card from a prescriber to a patient;

e) the patient in turn presenting the activated product trial card to a participating pharmacy;

f) validating the activated product trial card at the pharmacy by the pharmacy communicatively linking the presented product trial card with the central computing station and verifying that the presented product trial card has in fact been activated and not previously validated;

g) after validating the presented product trial card, the pharmacy then dispensing the approved pharmaceutical trial product to the patient; and h) periodically accounting to the participating pharmacies for pharmaceutical trial product dispensed in accordance with the records of the database associated with the central computing system.

2. The method of claim 1 wherein the product trial cards when delivered to a prescriber are in an unactivated state and wherein the activation of the product trial cards takes place while said cards are in the possession of a prescriber.

3. The method of claim 2 further including the step of issuing an authorization card to the participating prescribers and wherein activation of the product trial card is conditioned upon respective prescribers establishing authorization.

4. The method of claim 3 including the step of establishing prescriber authorization by communicatively linking a prescriber's authorization card with the central computing station and verifying the authenticity of the prescriber's authorization card.

5. The method of claim 4 wherein the product trial cards are activated after prescriber authorization has been established and wherein the product trial cards are activated by communicatively linking the respective cards with the central computing station wherein the product trial cards are authenticated and encoded information associated with the respective product trial cards are recorded in a database associated with the central computing station.

6. The method of claim 5 wherein the step of activating the product trial cards includes issuing to the prescriber an approval code for each product trial card activated.

7. The method of claim 6 including the step of physically recording the issued approval code for each product trial card on the product trial card itself.

8. The method of claim 7 including the step of the prescriber signing each activated product trial card.

9. The method of claim 3 including the step of issuing an authorization card to each participating pharmacy and wherein validation of the product trial cards is conditioned upon the validating pharmacy first establishing authorization.

10. The method of claim 9 including the step of establishing pharmacy authorization by communicatively linking a pharmacy's authorization card with the central computing station and verifying the authenticity of the pharmacy's authorization card.

11. The method of claim 10 wherein the step of validation includes communicatively linking each product trial card presented by a patient to a pharmacy with the central computing station and verifying that the presented product trial card has been activated and not previously validated.

12. The method of claim 11 including the step of issuing a pharmacy approval code in response to the presented product trial card being validated.

13. The method of claim 12 including the step of the pharmacy physically recording the pharmacy approval code on the presented product trial card as a part of the validation procedure.

14. The method of claim 13 including the further step of the pharmacy actually signing the product trial card prior to or at the time of dispensing the trial pharmaceutical product to the patient.

15. The method of claim 1 including the step of accounting to the pharmacies for trial product dispense based on the records of the database associated with the central computing station.

16. The method of claim 9 wherein a program manager manages the distribution of pharmaceutical trial product and wherein the program manager upon receiving data stored in the database associated with the central computing station then authorizes replacement of pharmaceutical product to the individual participating pharmacies through wholesalers.

17. The method of claim 16 further including the step of authorizing dispensing fees to the participating pharmacies based on the recorded pharmaceutical trial products dispensed by the pharmacies.

18. The method of claim 1 wherein the identifying information encoded on each product trial card includes product name, product size, product form and product quantity.

19. The method of claim 1 wherein the communication links between the participating prescribers, pharmacies and the central computing station are provided through a card reader terminal, and wherein communication is established between the respective product trial cards and the central computing station by the swiping of the product trial cards through the card reader terminal.

20. The method of claim 1 wherein each participating prescriber and pharmacy has access to a terminal that is communicatively linked to a central computing station, and wherein the method includes the step of the participating prescribers and pharmacies entering authorization information into their respective terminal and thereafter that information being uploaded into the central computing station where the entered authorization information is verified prior to the respective prescriber establishing activation and the respective pharmacies establishing validation.

21. The method of claim 20 wherein the participating prescribers and pharmacies are issued an authorization media that is designed to be read by the respective terminals and wherein the step of entering authorization information includes the step of the respective prescribers and pharmacies entering their respective authorization media into their respective terminal and wherein encoded information associated with the authorization media that is stored into the respective terminal.

22. The method of claim 21 wherein the step of activating the product trial media includes entering data associated with the product trial media into a terminal and thereafter uploading data from the product trial media from the terminal to the central computing station.

23. A method of dispensing, tracking and managing pharmaceutical trial products utilizing prescribers, pharmacies, and a system including a central computing station and database, comprising the steps of:

a) forming a trial product media and encoding that media with information that identifies a particular trial pharmaceutical product;

b) issuing the trial product media to one or more prescribers;

c) activating the trial product media by a prescriber communicatively linking the trial product media to the central computing station wherein the central computing station records encoded information from the trial product media into a database associated with the central computing station and thereby activates the trial product media;

d) the step of activating the product trial media including entering data associated with the product trial media into a terminal and thereafter uploading data associated with the product trial media from the terminal to the central computing station;

e) transferring the activated product trial media from a prescriber to a patient;

f) the patient then presenting the activated product trial media to a pharmacy;

g) validating the product trial media at the pharmacy by communicatively linking the presented product trial media with the central computing station which determines if the presented product trial media has in fact been activated by a prescriber and if activated, the central computing station approves dispensing of the pharmaceutical product identified and authorized by that product trial media;

h) the step of validating the product trial media including entering data from the activated product trial media into a terminal and uploading that data from the terminal to the central computing station;

i) after validating the presented product trial media, dispensing the approved pharmaceutical trial product to the patient; and j) periodically accounting to the participating pharmacies for pharmaceutical trial product dispensed in accordance with the records of the database associated with the central computing station.

24. The method of claim 23 wherein activation of the product trial media is conditioned upon the activating prescriber being an authorized prescriber, and wherein validation and dispensing of the pharmaceutical trial product is conditioned upon the validating and dispensing pharmacy being an authorized pharmacy.

25. The method of claim 24 wherein authorization for both prescribers and pharmacies is established in part at least by issuing a uniquely identifying authorizing media to each participating prescriber and pharmacy and wherein the step of authorization entails prescribers and pharmacies establishing a communication link between the issued authorizing media and the central computing station wherein the central computing station effectively scans the issued authorizing media so as to authenticate the same.

26. The method of claim 25 wherein participating prescribers and pharmacies are provided with a communication terminal for communicating with the central computing station, and wherein prescriber and pharmacy authorization is further conditioned upon the initialization of the communication terminal associated with respective prescribers and pharmacies.

27. The method of claim 23 including recording in the database associated with the central computing station selected encoded information associated with the product trial media both during the activating and validating steps of the method.

28. The method of claim 23 including the step of issuing authorizing media to participating prescribers and pharmacies and wherein the authorizing media includes encoded identifying information that identifies particular prescribers and pharmacies, and wherein the steps of activating and validating the product trial media include recording in the database associated with the central computing station encoded information on the authorizing media of the prescribers and pharmacies.

29. The method of claim 28 including the step of conditioning the activating step on the prescriber communicating a unique identification code to the central computing station and further conditioning the validating step on the pharmacy communicating a unique identification code to the central computing station.

30. The method of claim 28 wherein the system further includes a series of terminals located at prescriber and pharmacy sites with each terminal being communicatively linked to the central computing station and wherein both the activating and validating steps of the method are conditioned upon the initialization of the terminal of any participating prescriber and pharmacy.

* * * * *